United States Patent [19]

Weidig

[11] Patent Number: 4,524,222

[45] Date of Patent: Jun. 18, 1985

[54] ALKYLATED PHENOL PURIFICATION

[75] Inventor: Charles F. Weidig, Baton Rouge, La.

[73] Assignee: Ethyl Corporation, Richmond, Va.

[21] Appl. No.: 574,134

[22] Filed: Jan. 26, 1984

[51] Int. Cl.³ .............................................. C07C 29/74
[52] U.S. Cl. .................................... 568/711; 568/710; 568/749
[58] Field of Search ............... 568/710, 749, 758, 711

[56] References Cited

U.S. PATENT DOCUMENTS

| | | | |
|---|---|---|---|
| 2,192,197 | 3/1940 | Mills et al. | 568/711 |
| 2,256,195 | 9/1941 | Filbert | 568/711 |
| 2,311,283 | 2/1943 | Roblin | 568/711 |
| 2,325,753 | 8/1943 | Dolt | 568/711 |
| 2,331,244 | 10/1943 | Strickland | 568/758 |
| 2,392,859 | 1/1946 | Meuile | 568/711 |
| 2,632,027 | 4/1953 | Smith | 568/758 |
| 2,810,767 | 10/1957 | Clarke et al. | 568/711 |
| 2,831,898 | 4/1958 | Ecke | 568/789 |
| 3,202,719 | 8/1965 | Jones | 568/758 |
| 3,442,958 | 5/1969 | Choo | 568/758 |
| 4,439,374 | 3/1984 | Burton et al. | 568/711 |

FOREIGN PATENT DOCUMENTS

| | | | |
|---|---|---|---|
| 2153329 | 4/1972 | Fed. Rep. of Germany | 568/758 |
| 2644318 | 4/1978 | Fed. Rep. of Germany | 568/749 |

OTHER PUBLICATIONS

Zieborak et al., "Chemistry and Industry," No. 13, Jul. 4, 1983, pp. 516–518.

Primary Examiner—Werren B. Lone
Attorney, Agent, or Firm—Donald L. Johnson; John F. Sieberth; John F. Hunt

[57] ABSTRACT

Dinitro alkyl phenols are produced free of tar when the precursor orthoalkylphenol is contacted with a molecular sieve prior to sulfonation, nitration, and air drying. The dinitro alkylphenols produced are free of tars or similar resins and avoid processing problems that are shown in impure prior art products.

14 Claims, No Drawings

ALKYLATED PHENOL PURIFICATION

BACKGROUND OF THE INVENTION

1. Field of the Invention

The present invention is related to the production of dinitro-o-alkylphenols and the purification of precursor o-alkylphenols.

2. Description of the Prior Art

Dinitro-o-sec-butylphenol is a commercial herbicide. It can be made by reacting o-sec-butylphenol with concentrated sulfuric acid to form a sulfonated o-sec-butylphenol which can be reacted with aqueous sodium nitrate to form mainly 2,4-dinitro-6-sec-alkylphenol. This reaction sequence as applied to higher alkylphenols is described in U.S. Pat. No. 2,810,767. It is also known to use nitric acid in place of the aqueous sodium nitrate as the nitrating agent.

Although the above reaction sequence works well with highly purified colorless o-sec-butylphenol, it is not completely satisfactory with less pure o-sec-butylphenol which is slightly yellow to amber or brown in color. With such impure o-sec-butylphenol starting material, the final dried product after the nitration is dark in color and contains a tar-like residue. Thus, a need exists to render impure o-sec-butylphenol satisfactory for sulfonation and nitration without an expensive purification procedure.

The various o-alkylphenols made by various methods often contain impurities which may result in the formation of undersirable by-products, especially tars. One such method which may result in the production of an o-alkylphenol containing a material which results in the production of tars when processed to make dinitro-o-sec-butylphenol as described above is the orthoalkylation of phenol with butene using an aluminum phenoxide or gammalaumina catalyst. One such process for preparing such an o-alkylphenol is described in U.S. Pat. No. 2,831,898.

SUMMARY OF THE INVENTION

The present invention is directed to the correction of tar formation in a sulfonation and nitration process. It has now been discovered that impure discolored o-sec-butylphenol and other o-alkylphenols can be successfully sulfonated and nitrated by reaction with concentrated sulfuric acid and then nitric acid and subsequently air dried to form a tar free product which does not foul equipment or corrode storage containers for the dinitro-o-alkylphenol such as results when the tars remain in the product.

The present invention is a process for the production of a tar free dinitro-o-alkylphenol, said process comprising reacting an impure o-alkylphenol with concentrated sulfuric acid to produce a sulfonated o-alkylphenol and then reacting the sulfonated o-alkylphenol with nitric acid, the improvement comprising contacting said o-alkylphenol with a molecular sieve material to purify said o-alkylphenol. The present invention is also a process for treating an impure o-alkylphenol to suppress its normal tendency to yield tarry impurities when subjected to sulfonation with sulphuric acid followed by nitration, which process comprises contacting said impure o-alkylphenol with a molecular sieve material so that such tar forming tendency is suppressed.

DESCRIPTION OF THE PREFERRED EMBODIMENTS

A preferred embodiment of the invention is a process of contacting an impure o-alkylphenol, otherwise tending to form tars when subjected to sulfonation with sulphuric acid followed by nitration, with a molecular sieve. A preferred embodiment of the present invention is also an improvement in the process of sulfonating and nitrating an impure o-alkylphenol to form a tar free dinitro-o-alkylphenol by first contacting the o-alkylphenol precursor with a molecular sieve. According to the present invention at least about 1 part by weight of the molecular sieve is used for contacting about 50 parts by weight of the impure o-alkylphenol to render it suitable for sulfonation and nitration resulting in the production of dinitro-o-alkylphenol without tars.

The tar free products of the present invention are useful as herbicides as disclosed in U.S. Pat. No. 2,392,859. Accordingly, a further embodiment of the invention is a process for making 2,4-dinitro-6-alkylphenol, said process comprising (a) contacting about 1 part by weight of a synthetic or natural crystalline metal alumino-silicate that has been activated for adsorption by removing the water of hydration with about 50 parts by weight of the precursor o-alkylphenol, (b) reacting said o-alkylphenol that has been contacted with the molecular sieve with concentrated sulfuric acid in an amount of at least about 2 moles of sulfuric acid per mole of said o-alkylphenol at a temperature of about 30°–150° C. to form sulfonated o-alkylphenol, and then (c) reacting said sulfonated o-alkylphenol with a nitrating agent selected from the group consisting of nitric acid, and salts thereof in an amount of at least about 2 moles of nitrating agent per mole of said o-alkylphenol at a temperature of about 30°–150° C. and (d) recovering a dinitro-o-alkylphenol product of high purity being substantially free of insoluble tar. Optionally, the recovered dinitro-o-alkylphenol product of high purity is air dried, preferably at about 100° C. to speed the air drying of the recovered product.

A broad range of o-alkylphenol can be used in the process. The alkyl group can be primary, secondary and tertiary. Preferably, the alkyl is primary or secondary because tertiary alkyl groups are susceptible to dealkylation in the process. The alkyl groups can contain from 1-20 or more carbon atoms. Examples of these are o-cresol, o-ethylphenol, o-isopropylphenol, o-(n-hexyl)phenol, o-(n-octyl)phenol, o-(n-octadecyl)phenol, o-(n-eicosyl)phenol, o-(1-methylundecyl)phenol, o-sec-amylphenol, o-sec-octylphenol, o-sec-dodecylphenol, o-sec-eicosylphenol, and the like.

More preferably, the o-alkyl group is a sec-alkyl containing about 3-12 carbon atoms. These include o-isopropylphenol, o-sec-butylphenol, o-(1-methylphenyl)phenol, o-(1-methylheptyl)phenol, o-(1-methylundecyl)phenol, o-(1-ethylbutyl)phenol, and the like.

The most important o-alkylphenol is o-sec-butylphenol because of its usefulness in making dinitro-o-sec-butylphenol, an important herbicide.

Molecular sieves have been described as unique adsorbents usually used for drying streams. They are generally described as synthetic or naturally occuring crystalline metal alumino-silicates. Usually, the synthetic molecular sieves have been activated for adsorption by removing their water of hydration. Thus, these structures are normally designed for the removal of water from process streams but Applicant has found that they may be used for the contacting described herein to afford a dinitro-o-alkylphenol product which is completely tar free, thus avoiding further processing problems with equipment using a herbicide and avoiding problems of storage container corrosion caused by tars otherwise present in the product. The pores of the molecular sieves are generally of precise uniformity and molecular dimension and are generally selective for polar or polarizable molecules.

The molecular sieves belong to a class of compounds known as zeolites. Since the molecular sieves are generally very chemically stable they are useful for collection of water from gaseous or other product streams and have typical pore dimensions of 3 to 5 Angstroms. In the 5 Angstroms variety of the molecular sieve, calcium cations replace some of the sodium cations in a three dimensional interconnecting network structure of silicon alumina tetrahedra. The molecular sieves are also typically used for removal of such simple compounds as hydrogen sulfide and carbon monoxide.

The present invention is designed to provide a relatively inexpensive process for the purification of a precursor o-alkylphenol so as to provide a dinitro-o-alkylphenol product, commonly used as a herbicide, which does not change substantially in pH, apparently caused by the presence of tars in the product from an unpurified source of o-alkylphenol. The increase in pH of such an dinitro-o-alkylphenol product can cause problems with corrosion of containers for the product and with contamination of fouling of machinery using the product as a herbicide or for another use.

Typically, the dinitro-o-alkylphenol product is air dried at about 100°–105° C. to blow off both water and some of the residual acid used in the production of the dinitro-o-alkylphenol. Care should be exercised in making a clean cut between the aqueous and organic phases which remain after production of the product. If too much acid remains in the organic layer, then excessive drying may be required and the formation of other by-products may result.

The present invention is also designed to provide an economical process for purification of o-alkylphenols so as to suppress its normal tendency to produce tars exhibited upon sulfonation and nitration. The purification is accomplished by contacting the impure o-alkylphenol, especially o-sec-butylphenol with a molecular sieve. Of course, the so purified o-alkylphenols are usable for other purposes but their tendency to form tars as displayed in sulfonation and nitration is eliminated.

The most preferred molecular sieve of the present invention is that of the 5 Angstrom pore size.

Regeneration of the molecular sieve is necessary after about 50 parts by weight of an o-alkylphenol such as o-sec-butylphenol is contacted per 1 part by weight of molecular sieve. This is a rule of thumb measurement only and I carried out experiments to determine the approximate breakthrough point wherein the molecular sieve becomes saturated. Regeneration can be achieved by heating, chemical treatment, or both.

EXAMPLE 1

Two gallons of o-sec-butylphenol prepared by the aluminum phenoxide catalyzed reaction of butene 1 and phenol were flash distilled at 160° C. and 90 millimeters mercury and then passed through 50 grams of 5 Angstrom molecular sieve sold by J. T. Baker Chemical, with cuts being taken at approximately every 16 ounces. Thereafter, the samples of o-sec-butylphenol which had been contacted with the 5 Angstrom molecular sieve at ambient temperature were used in a sulfonation and nitration step to produce dinitro-o-sec-butylphenol. Seventeen of the samples were taken. The sulfonation and nitration of the o-sec-butylphenol from the first and fifth samples produced a good dinitro-o-sec-butylphenol product with no tars after air drying. In comparison, the tenth and seventeenth samples of the o-sec-butylphenol precursor resulted in products which contained tars after air drying.

A similar experiment was carried out on a larger scale but contacting the o-sec-butylphenol with the molecular sieve at about 80° C. The results were substantially the same with a very slight residue of tar after the Ω10 cut. Analysis of the impure o-sec-butylphenol revealed the presence of the compound 2,3-dimethylbenzofuran (DMBF). While this compound is a primary suspect for formation of tars and other side reactions which may result in tars the exact involvement of the compound is not known other than the fact that up to about 0.3 weight percent of the compound may be present.

The o-alkylphenol of the present invention may be passed over the molecular sieve or contacted therewith by any of several methods which economically provide a purification of the o-sec-butylphenol. A column or tube of the molecular sieve may be used and the o-alkylphenol passed therethrough. Usually, merely passing the o-alkylphenol over the molecular sieve is sufficient. With regard to the carrying out of the sulfonation and nitration steps of the invention, many variations are possible. The sulfonation temperature should be high enough to cause the sulfonation to proceed but not so high as to cause excessive decomposition of the reactants or products. A useful temperature range in which to experiment is about 10°–200° C. A more preferred temperature range is about 30°–150° C. Excellent results have been achieved with o-sec-butylphenol at about 70°–95° C.

Concentrated sulfuric acid is used in the sulfonation. Preferably, the sulfuric acid is at least 90 weight percent $H_2SO_4$ and more preferably at least 95 weight percent $H_2SO_4$. Optionally oleum may be used in the sulfonation. Oleum can contain up to about 30 percent or more sulfur trioxide.

The amount of sulfuric acid should be sufficient to provide at least about 2 moles of $H_2SO_4$ per mole of o-alkylphenol. A useful range is about 2–5 moles of sulfuric acid per mole of o-alkylphenol. A more preferable range is about 2.5–3.5 moles of sulfuric acid per mole of o-alkylphenol. Good results have been achieved using 2.3 moles of sulfuric acid per mole of o-sec-butylphenol.

The sulfonation time is not critical. This depends to some extent on the cooling capacity available because the reaction is exothermic. Good results can usually be attained by adding the o-alkylphenol containing the polybasic acid to the stirred concentrated sulfuric acid over a period of about 0.25–8 hours followed by a post-addition stirring period of about 0.24–4 hours.

The benefits of the improved process are most apparent when the o-alkylphenol is impure. The impurities present are believed to be oxidation products although knowledge of the chemical identity of the impurities is not crucial to the successful use of the process. Impure o-alkylphenol is readily recognized by its yellow to amber color even though it might assay as high as 99 weight percent o-alkylphenol. For the purpose of the process, "impure" o-alkylphenol is that which contains tar-forming ingredients whereas "pure" o-alkylphenol does not contain such tar-forming contaminants.

EXAMPLE II

A 5A molecular sieve supplied by J. T. Baker Chemical was heated under vacuum at 80° C. for 2 hours. A liquid chromatographic column 10" long and 0.8" in diameter with an approximately 100 mL solvent reservoir was charged with 50 g molecular sieve. O-sec-butylphenol (ambient temperature) was poured into the column and 16-ounce fractions were collected. A 500 mL 3-neck round bottom flask equipped with a pressure equalizing addition funnel, an overhead stirrer assembly, a thermometer with attached Thermowatch TM controller, and a heating mantle was charged with reagent grade sulfuric acid (123 mL). The acid was heated to 50° C. and o-sec-butylphenol (116 mL) which has been contacted with a few ounces of 5 Angstrom molecular sieve was added dropwise over a 10 to 20 minute period while maintaining the pot temperature below 80° C. Upon completion of the o-sec-butylphenol addition, the reaction mixture was heated to 95° C. and held for 2 hours.

A 2 L 3-neck round bottom flask which has a small bore stopcock at the bottom, was equipped with an overhead stirrer assembly, a thermometer with attached Thermowatch controller and the appropriate heating mantle. The flask was charged with water (581 mL) and reagent grade nitric acid (179 mL) and the solution was heated to 50° C. The sulfonate mixture prepared above was transferred to the addition funnel and added over a 1–1.5 hour period while maintaining the pot temperature below 80° C. Upon completion of sulfonate addition, the reaction mixture was heated to 100° C. and held for 2 hours. The addition funnel was removed and replaced with a reflux condenser. The gases evolved during the nitration were trapped in a large volume of dilute caustic. After two hours the reaction mixture was cooled to 65° and the organic layer was drawn off the bottom through the stopcock.

A 200 mL round bottom thermowell flask was equipped with a tape heated 3-way connecting tube, a heating mantle, a magnetic stirring bar, a magnetic stirrer and a thermometer which was attached to a Thermowatch TM controller. The air used for drying was controlled with a valve and the flow rate was measured with a flow meter. Rubber tubing from the flow meter was connected with a polytetrafluoroethylene needle which in turn was sealed through one of the connecting tube joints and pushed down below the surface of the DNBP. To the other joint of the connecting tube was attached a small vacuum jacketed Claisen distillation head. Attached to the claisen head was a thermometer to measure overhead temperatures and a condenser with an appropriate distillation receiver. The air and gases blown out during the dinitrobutylphenol (DNBP) drying step were discharged into a large volume of water.

The DNBP was heated while stirring in the drying apparatus. When the pot temperature reached about 90° C., the air was turned on and a flow rate of 10 SCFH was maintained throughout the drying step. The drying temperature was maintained at 100±5° C. for 15–20 minutes. The hot DNBP was then discharged into a sample container. The concentration of residual acid was too small (estimated to be 1% based on larger scale runs) to be cut at this step.

DNBP can be solidified by seeding with crystals. The crystallization process occurs rapidly with seeding but may take months without seeding. The residual acid can be seen as a liquid after solid DNBP is formed.

The process of the present invention affords a relatively inexpensive method for purification of o-alkylphenols for their use in a sulfonation and nitration reaction to produce a dinitro-o-alkylphenol which is free of tars. Applicant's employer has spent over one hundred thousand dollars in equipment and man-hours to find an economical purification process resulting in tar-free dinitro orthoalkylphenol. Other methods of washing, crystallization, and the like have been attempted for the purification of such alkylphenols but none have proven to be so economical as the present invention and none have proven to work as well as the resent invention for producing a tar free dinitro-o-alkylphenol product, especially dinitro-o-sec-butylphenol.

In the process of the present invention, the nitric acid concentration is not critical. The concentration can range from about 10–70 weight percent $HNO_3$. A more preferable concentration range is about 15–50 weight percent $HNO_3$. Best results with sulfonated o-sec-butylphenol have been achieved using a nitric acid concentration of about 16 weight percent.

The amount of nitric acid should be an amount which provides at least 2 moles of nitric acid per mole of original o-alkylphenol because the product target is dinitro-o-alkylphenol. A useful range is about 2–5 moles of nitric acid per mole of original o-alkylphenol and more preferably about 2.5–3.5 moles of nitric acid per mole of original alkylphenol.

The nitrogen temperature can vary over a wide range. A useful range is about 20° C. up to reflux. A more preferred range is about 35°–100° C. Usually the reaction is started by feeding the sulfonated o-alkylphenol to the nitric acid at about 35°–65° C. and then allowing the heat of the reaction to increase the temperature to about 90°–100° C. After completion of the addition, the mixture is preferably stirred at elevated temperatures (approximately 90°–100° C.) for a period sufficient to complete the nitration (approximately 1–4 hours).

Following the nitration, the reaction mixture is allowed to separate and the acid layer is subjected to proper disposal methods. The organic layer may be water washed and dried. Washing is not required and a useful product can be obtained by merely blowing air or more gas through the liquid at elevated temperature (e.g. 100° C.) to drive off water.

Alternatively, a nitric acid salt can be used as the nitrating agent. Preferred salts are the alkali metal salts such as sodium or potassium nitrate. These are used in the form of aqueous solutions. The amount of nitrate salt should provide at least 2 moles of nitrate anion per mole of original o-alkyphenol and more preferably about 2.5–3.5 moles per mole of original alkylphenol. The amount of water used to make the solution can vary over a wide range. Preferably, the nitrate salts concentration should be about 20–60 weight percent and more preferably about 30–50 weight percent.

The nitration is conducted in the same manner as with nitric acid by adding the crude sulfonated o-alkylphenol to the aqueous nitrate salt. Addition can start at about 35°–65° C. and the temperature allowed to increase to about 90°–100° C. A postaddition reaction time of about 1–4 hours at 90°–100° C. is beneficial.

Product is recovered in the same manner as when using nitric acid by allowing the water phase to separate and removing it. The organic phase can be water washed but this is not critical. The orgaic phase can be dried by heating while passing air or an inert gas through it or by applying vacuum.

Many variations of the present invention are possible by exchanging certain features of the present invention without departing from the scope or spirit thereof as defined by the appended claims.

I claim:

1. In a process for the production of a tar free dinitro-o-sec-alkylphenol, said process comprising reacting an impure o-sec-alkylphenol with concentrated sulfuric acid to produce a sulfonated o-sec-alkylphenol and then reacting the sulfonated o-sec-alkylphenol with nitric acid, the improvement comprising contacting said o-sec-alkylphenol with a molecular sieve material to purify said o-sec-alkylphenol.

2. The improvement of claim 1 wherein said dinitro o-sec-alkylphenol is air dried after nitration.

3. The process of claim 2 wherein the dinitro o-sec-alkylphenol is air dried at about 100° C.

4. The process of claim 1 wherein said o-sec-alkylphenol is o-sec-butylphenol.

5. The process of claim 1 wherein at least about 1 part by weight of the molecular sieve is used for contacting 50 parts by weight of said o-sec-alkylphenol.

6. The process of claim 1 wherein said molecular sieve is a crystalline metal alumino-silicate that has been activated for adsorption by removing the water of hydration.

7. The process of claim 1 wherein said impure o-sec-alkylphenol contains 2,3-dimethylbenzofuran.

8. The process of claim 7 wherein said o-sec-alkylphenol is o-sec-butylphenol.

9. The process of claim 4 wherein said o-sec-butylphenol is prepared by alkylation of phenol with butene using an aluminum or aluminum phenoxide catalyst.

10. The process of claim 1 wherein said molecular sieve has a pore size of about 5 Angstroms.

11. The process of claim 4 wherein said molecular sieve has a pore size of about 5 Angstroms.

12. The process of claim 10 wherein the crystalline metal alumino silicate has a three dimensional interconnecting network structure of silica and alumina tetrahedra with calcium cations substituted for the sodium cations.

13. A process for treating an impure o-sec-alkylphenol to suppress its normal tendency to yield tarry impurities when subjected to sulfonation with sulphuric acid followed by nitration, which process comprises contacting said impure o-sec-alkylphenol with a molecular sieve material so that such tar forming tendency is suppressed.

14. The process of claim 12 wherein said impure o-sec-alkylphenol is o-sec-butylphenol.

* * * * *

UNITED STATES PATENT AND TRADEMARK OFFICE
CERTIFICATE OF CORRECTION

PATENT NO. : 4,524,222

DATED : JUNE 18, 1985

INVENTOR(S) : CHARLES F. WEIDIG

It is certified that error appears in the above-identified patent and that said Letters Patent is hereby corrected as shown below:

Column 1, line 39, reads "gammalaumina" and should read -- gamma-alumina --.

Column 2, line 43, reads "secondary and" and should read -- secondary or --.

Column 2, line 55, reads "o-(1-methylphenyl)-" and should read -- o-(1-methylpentyl) --.

Column 3, line 28, reads "an" and should read -- a --.

Column 3, line 30, reads "of"(1st occurrence) should read --or--

Column 4, line 14, reads "$\Omega$" and should read -- # --.

Column 4, line 59, reads "0.24-4" and should read -- 0.25-4 --.

Column 6, line 16, reads "resent" and should read -- present --.

Column 6, line 34, reads "nitrogen" and should read -- nitration --.

UNITED STATES PATENT AND TRADEMARK OFFICE
CERTIFICATE OF CORRECTION

PATENT NO. : 4,524,222

DATED : JUNE 18, 1985

INVENTOR(S) : CHARLES F. WEIDIG

It is certified that error appears in the above-identified patent and that said Letters Patent is hereby corrected as shown below:

Column 7, line 4, reads "orgaic" and should read -- organic --.

Signed and Sealed this

First Day of October 1985

[SEAL]

Attest:

DONALD J. QUIGG

Attesting Officer

Commissioner of Patents and Trademarks—Designate